United States Patent
Gonzalez, Jr.

(10) Patent No.: US 9,167,878 B2
(45) Date of Patent: Oct. 27, 2015

(54) SYSTEM AND METHOD FOR DIVIDING HAIR USING WATER SOLUBLE DIVIDERS DURING THE PROCESS OF HAIR COLORING OR HIGHLIGHTING TREATMENT

(71) Applicant: Ruben Gonzalez, Jr., Austin, TX (US)

(72) Inventor: Ruben Gonzalez, Jr., Austin, TX (US)

( * ) Notice: Subject to any disclaimer, the term of this patent is extended or adjusted under 35 U.S.C. 154(b) by 0 days.

(21) Appl. No.: 14/196,825

(22) Filed: Mar. 4, 2014

(65) Prior Publication Data

US 2015/0250284 A1    Sep. 10, 2015

(51) Int. Cl.
| | |
|---|---|
| *A61K 8/18* | (2006.01) |
| *A61Q 5/08* | (2006.01) |
| *A61Q 5/10* | (2006.01) |
| *A45D 19/18* | (2006.01) |
| *A45D 2/00* | (2006.01) |
| *A45D 19/00* | (2006.01) |
| *A45D 7/04* | (2006.01) |
| *A45D 7/00* | (2006.01) |
| *A61K 8/02* | (2006.01) |

(52) U.S. Cl.
CPC ............ *A45D 19/0025* (2013.01); *A45D 7/045* (2013.01); *A45D 2007/001* (2013.01); *A45D 2019/0066* (2013.01); *A45D 2019/0091* (2013.01); *A61K 8/0208* (2013.01)

(58) Field of Classification Search
CPC ............. A45D 19/00; A45D 19/0008; A45D 19/0016; A45D 19/0025; A45D 2019/0041; A45D 2019/0066; A45D 2019/0083; A45D 2019/0091; A45D 2007/001; A45D 7/02; A45D 7/04; A45D 7/045; A45D 7/06; A45D 7/065; A45D 2019/0058; A45D 19/18; A61Q 5/08; A61Q 5/10; A61K 8/0208
USPC ......... 132/208, 200, 210, 211, 212, 108, 163, 132/221, 222, 240, 241, 270, 333, 902; 383/1; 8/405
See application file for complete search history.

(56) References Cited

U.S. PATENT DOCUMENTS

| | | | | |
|---|---|---|---|---|
| 3,431,166 | A * | 3/1969 | Ishibashi et al. | 162/135 |
| 3,859,125 | A * | 1/1975 | Miller et al. | 428/511 |
| 4,655,377 | A * | 4/1987 | Orangeo et al. | 225/48 |
| 4,672,983 | A | 6/1987 | Nath et al. | |
| 5,056,539 | A | 10/1991 | Abramson | |
| 5,064,470 | A | 11/1991 | Scarpelli | |
| 5,121,762 | A * | 6/1992 | DiPinto et al. | 132/204 |
| 5,146,937 | A | 9/1992 | Lefebvre | |
| 5,196,149 | A | 3/1993 | Scarpelli | |
| 5,250,353 | A * | 10/1993 | Bartholomew et al. | 428/328 |
| 5,287,864 | A | 2/1994 | Gallo | |
| 5,349,970 | A | 9/1994 | Razzouq | |
| 5,816,268 | A | 10/1998 | Awaijane | |

(Continued)

FOREIGN PATENT DOCUMENTS

GB    2513315 A  * 10/2014

*Primary Examiner* — Vanitha Elgart
(74) *Attorney, Agent, or Firm* — M. Susan Spiering; Ferrells, PLLC

(57) ABSTRACT

Disclosed is a new use for water soluble cellulosic paper, which is triangular, planar, foldable, biodegradable, and non-toxic to the user and environment. It has been found that water soluble paper is effective as a substitute for foil in the hair color-highlighting process. Numerous benefits have been found with this invention, among them: it is eco-friendly, more comfortable to the user than foil, leaves hair conditioned and shiny, and does not damage hair as foil tends to.

5 Claims, 1 Drawing Sheet

(56) References Cited

U.S. PATENT DOCUMENTS

| | | |
|---|---|---|
| 6,776,287 B1 | 8/2004 | Hinde et al. |
| 7,191,783 B2* | 3/2007 | Russell .................. 132/222 |
| 7,425,220 B2* | 9/2008 | Barrass et al. ............... 8/405 |
| 7,628,160 B2 | 12/2009 | Winup |
| 2003/0033678 A1* | 2/2003 | Schulze zur Wiesche et al. ........................... 8/405 |
| 2003/0059459 A1* | 3/2003 | Pyles ........................ 424/443 |
| 2003/0088925 A1* | 5/2003 | DeVoe et al. ................ 8/405 |
| 2004/0016206 A1* | 1/2004 | DeVoe et al. ............... 53/396 |
| 2005/0039768 A1* | 2/2005 | Winckels .................. 132/208 |
| 2007/0028939 A1* | 2/2007 | Mareri et al. .............. 132/221 |
| 2009/0226116 A1* | 9/2009 | Hill et al. ..................... 383/1 |
| 2011/0073129 A1* | 3/2011 | Russell ..................... 132/270 |
| 2011/0168203 A1* | 7/2011 | Ivanov ...................... 132/211 |
| 2013/0291885 A1* | 11/2013 | Sbordone .................. 132/270 |
| 2014/0000823 A1* | 1/2014 | Salminen ...................... 162/4 |

* cited by examiner

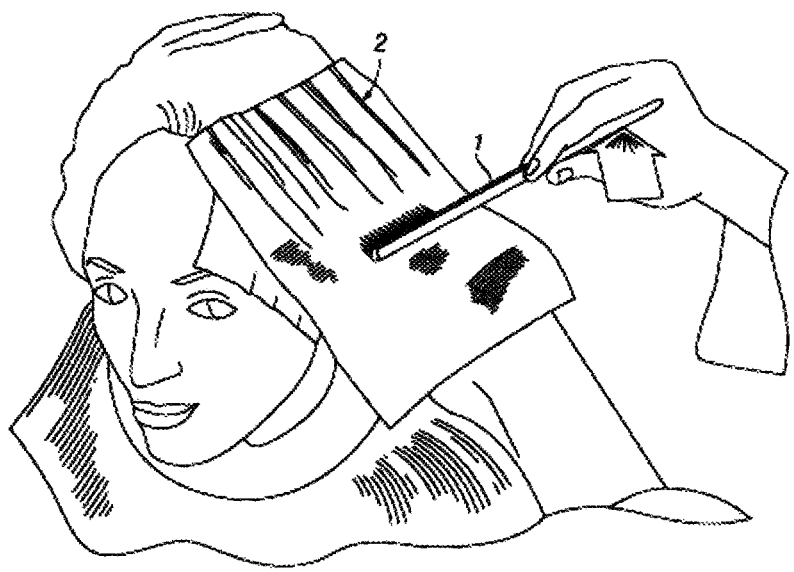

SYSTEM AND METHOD FOR DIVIDING HAIR USING WATER SOLUBLE DIVIDERS DURING THE PROCESS OF HAIR COLORING OR HIGHLIGHTING TREATMENT

BACKGROUND

1. Field of the Invention

This invention relates to the process for applying hair treatment, in particular color or highlights to hair.

2. Description of the Related Art

It is widely appreciated that both men and women wish to change their hair color from time to time, and for different underlying motivations. Professional services that provide hair coloring treatments and commercial off-the-shelf products that may be purchased and applied by the consumer are commonly provided throughout the United States and most communities internationally.

The process for applying a hair color treatment is well-established. However, the tools and products used in the hair color treatment process offer substantial room for improvement in their performance and their alignment with other values or priorities the user may hold, particularly environmental concerns and/or comfort during the hair color process.

Therefore, there continues to exist a need to replace incumbent products with new ones that offer additional dimensions of value to the user. In particular, the current trend or tool employed during the highlighting of hair is foil, which is well suited for improvement. Aluminum foil strips are employed to wrap sections of dyed hair within the foil. A hair stylist will typically isolate a portion of hair, place it on a foil strip, add hair treatment, i.e., color or hair dye to the hair and thereafter, wrap the hair within the foil so as the dye remains inside the now formed pocket of the foil. Upon completion of adding color and wrapping all desired hair strands in the foil strips, the user is placed under a dryer for a sufficient period of time to set the treatment or dye on the hair. This often is termed "cook" the color or treatment into the hair. Treatment herein is referred to any type of hair solution resulting in a modification to the hair such as a deep conditioner, cleanser, color or highlight, bleaching, straightening, curling, relaxing, or the like. The present invention has been found to be particular suited for highlighting hair, but other applications will be apparent to the user.

(The Problem) It has been found that during the hair dryer portion of the color treatment, the foil, as well as the hair, is heated and the foil transfers additional heat to the hair exacerbating the drying and damage to the hair. In addition, the aluminum or metallic foils currently in use are not environmentally friendly, and cannot be easily recycled in view of the chemical additive (ie., the hair color) present on the metallic foil. Disposal for current foil is through traditional trash-to-landfill procedures. Further, using foil in the coloring process often is uncomfortable for the user since it tends to pull the hair during use.

Various US and EP patents have published or issued relating to various techniques for coloring and treating hair, or for tools and kits utilized for hair coloring or hair highlighting. Patents include: U.S. Pat. No. 5,349,970 (method of foiling hair), U.S. Pat. No. 5,287,864 (frosting foils), U.S. Pat. No. 5,056,539 (process and product for highlighting hair using foil), U.S. Pat. No. 5,816,268 (hair highlighting method and apparatus using foil), U.S. Pat. No. 7,628,160 (tool and apparatus for use in hair coloring and other treatment foiling method), EP 1,562,454 (method and system for hair coloring and highlighting using a hair care kit), EP 2,005,854 (system for highlighting hair using device having 2 movably joined portions), EP 1,179,986 (application device for highlighting hair employing hair dye container).

Also existing are patents on the use of plastic sheets as alternatives to foil for highlighting hair. Patents include: U.S. Pat. No. 4,658,840 (flexible elastic plastic material having openings thereon and used during hair coloring), U.S. Pat. No. 5,146,937 (method of hair highlighting using polystyrene sheet), U.S. Pat. No. 4,672,983 (hair coloring using polyvinyl chloride, polyethylene, and polyproplylene).

It has been found that use of the plastic materials are not as efficient as foil and provide the stability of the color on the hair. Plastic is too flimsy to keep the hair stable. Plastic is used more for covering the head of hair to keep body heat in. Cling wrap can be used but, it is not ideal. It is too flimsy to work for highlighting. It is also messy and does not contain the color within its folds, causing color to be everywhere.

In view of the problems associated with use of foil, and the continuous issues associated with plastic, there exists a need for an alternative, or replacement for foil in the hair color/highlighting process.

SUMMARY

While the present invention is suitable for hair treatments of any type involving hair solution and the need for a foil, plastic, or sponge-like sheet, it will be described relative to hair color and highlighting of hair. This in no way limits the utility or applicability thereof. In an embodiment of the present invention, water soluble paper is positioned on the head of a person; a small amounts of hair is placed on the paper and a hair treatment solution is applied to the hair; the paper is then wrapped around the hair so as to form a pocket and maintain the solution within the paper; a sufficient period of time to allowed to pass so that the solution is allowed to set on the hair, ie., to color the hair; and, thereafter, the hair and paper is simultaneously rinsed with water, thereby removing the solution and the paper from the head of the person. The time to color the hair can be from about 30 minutes to about 45 minutes, or if there is extreme grey perhaps 60 minutes. Care must be taken so as to not damage the hair from overexposure to the dye.

The method optionally allows for the hair to be heated for a period of time sufficient to allow the treatment to set on the hair. Hair heating times can vary from about 10 minutes to about 45 minutes at approximately 85°-140° F. The time and temperature used vary depending on the treatment employed, i.e., hair conditioning, overall hair coloring, highlighting the hair etc. The heat source can also vary, for example, a hair dryer can be used, or alternatively, a heat lamp called a climizon. Those of skill in the art will recognize how to use the lamp and therefore details thereof are not described herein.

The present invention is an improvement on the current tools for hair highlighting and comprises use of water soluble paper as a replacement for foil. It has been found that water soluble paper, for example as that purchased by DayMark Technologies, or Edmund Scientific's, acts sufficiently like foil in that it can easily fold around hair strands, maintain the hair dye within the formed pocket of paper holding the dyed hair strand, be washed away during the rinse process, does not heat hair like foil, and the version purchased from Edwards Scientific appears to add conditioners to hair resulting in glossy hair strands. It is environmentally friendly since it completely dissolves in cold or warm water and can be disposed of as a liquid down the drain during the rinse phase of the highlighting treatment. No special treatment is needed in its disposal process.

Further aspects and advantages of the invention will become apparent from the discussion which follows.

BRIEF DESCRIPTION OF THE DRAWING

FIG. 1 is a perspective view showing the use of the water soluble paper by a hair colorist/stylist during a highlighting process.

DETAILED DESCRIPTION OF EMBODIMENTS

Described herein is a new use for water soluble paper.

The invention is described in detail below with reference to several embodiments and examples. Such discussion is for purposes of illustration only. Modifications to examples within the spirit and scope of the present invention, set forth in the appended claims, will be readily apparent to one of skill in the art. Terminology used throughout the specification and claims herein is given its ordinary meaning as supplemented by the discussion immediately below. As used in the specification and claims, the singular forms "a", "an" and "the" include plural references unless the context clearly dictates otherwise. Those with ordinary skill in the art will appreciate that the elements in the FIGURE are illustrated for simplicity and clarity and are not necessarily drawn to scale.

There may be additional components described in the foregoing application that are not depicted on one of the described drawing. In the event such a component is described, but not depicted in a drawing, the absence of such a drawing should not be considered as an omission of such design from the specification.

It should be observed that the present invention provides a water soluble paper for use in hair treatment and in particular for use during hair highlighting. Components of the invention have been represented where appropriate by conventional symbols in the drawings, showing only specific details that are pertinent for an understanding of the invention so as not to obscure the disclosure with details that will be readily apparent to those with ordinary skill in the art having the benefit of the description herein.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

Referring now to FIG. 1, illustrated is a hair stylist placing a hair solution on a user. The water soluble paper is placed on the head of the user whereby selected hair strands 2 are placed on the paper. The hair solution is then placed on the strands using a brush 1 over the paper, and the paper then folded to cover the now treated hair. The fold of the paper is such that a pocket forms so as to contain the hair solution.

Traditionally use of foil for treatments of hair has required removal of the foil from the user before rinsing any treatment or hair solution off of the user. This removal process step is time consuming and tends to pull the hair of the user causing discomfort.

The present invention allows the paper to remain on the scalp of the user the entire time of the treatment and when rinsing off the treatment, the paper dissolves and rinses down the drain along with the hair solution. There is no longer a need to remove the paper before the rinse cycle, or subject the user to the discomfort associated with the removal of the foil.

The objective or purpose of the invention is to provide an alternative to foil or metallic material that can be used by do-it-yourself consumers or professional hairstylists, and which is friendly to the environment, preferably washing away with water during the rinsing process, thus eliminating the trash-to-landfill procedure. Preferably, the paper is also efficacious in improving the appearance and texture of the hair, independent of the coloring chemicals or the shampoo or conditioner that may be used during the hair coloring process. It has been found that the paper is more comfortable for the user compared to foil usage.

(Physical Structure Of The paper) The paper is cellulose based and comprised of sodium carboxyl (sometimes referred to as "Carboxy") methyl cellulose and wooden pulp, or a reasonable alternative chemical composition that results in a water-soluble paper capable of performing the same function as foil during a hair treatment process. The paper functions much like foil in that it can be cut or folded, and separates the hair to be treated or colored from that which is not. The paper may be constructed in various dimensions to accommodate market expectations and user requirements. Typically the paper is planar, rectangular and of varying lengths sufficient to cover the hair to be treated, but generally from about 6 to about 12 inches in length, and about 4 to 6 inches in width. The paper is non-toxic and biodegradable, hence environmentally friendly.

Those skilled in the art will recognize that while a cellulose based paper is described herein, paper which is water soluble, foldable, non-toxic and biodegradable, and non-cellulose based, may be used for hair treatment purposes described herein.

The inventive paper may contain a plurality of additive chemicals, of natural or synthetic composition, manufactured into the water soluble paper for the purpose of delivering additional benefits to the hair, such as additional sheen or additional softness. This includes but is not limited to hair conditioner.

Products that perform the same function when human hair is colored are typically made from aluminum foil, plastic, or mesh paper and can be purchased from a variety of manufacturers throughout the world in different thicknesses and lengths. They are marketed under varying brand names, such as Armstrong Mcall, RDA, Salon Source.

A perceived benefit of the foil is its ability to conduct heat evenly, which is important in the hair coloring or highlighting process. However, there is no indication that the inventive water soluble paper is inferior to the foil in this regard, and to the contrary, has been found to dissipate heat away from the hair, eliminating or minimizing excess heat from causing damage or drying to the hair strands. Repeated experiments demonstrated the colored or highlighted hair was properly colored or protected from the hair solution color, and the sheen and softness of the hair were both enriched to the customer's delight. This was a surprising finding in view of industry standards and procedures generally used by those skilled in the art.

Traditional procedure performed with foil involves the use of a hair dryer. The inventive paper has been found to achieve better results when a dryer is not used, but instead the hair solution is combined with a climizon, which is like a hair heater.

The invention has shown to be safe to use and non-flammable when exposed to high heat, such as the heat used in a professional hair salon during a hair coloring or highlighting treatment.

Some products utilizing the water soluble paper properties afforded by Sodium CarboxyMethyl Cellulose and wooden pulp combinations may be subject to preexisting patent protection and include but are not limited to the following products:
1. Envelopes
2. Sachets
3. Tubing
4. Packaging
5. Bags
6. Labels
7. Copy Paper
8. Party Supplies
9. Paper Plates & Cups
10. Pouches However, it had not been found that the water soluble paper of this present invention was suitable for hair treatment uses, nor was it suggested that this could be an application of the paper. The hair industry at the time did not consider water soluble paper for hair treatments. Water-soluble paper products derived from chemicals other than Sodium Carboxy Methyl Cellulose may be purchased from a plethora of manufacturers located in various countries. This is not the subject of the present invention. The present invention is focused on use of water soluble paper useful in the hair treatment industry. Water soluble packaging is frequently based on polymeric material having elastic properties. These types of plastic products will not work in the hair coloring industry based on the difficulty of folding a plastic sheet around strands of colored hair, or maintaining a fold for a sufficient period of time to keep the hair treating solution therein.

(Unique Attributes) Unique attributes of the water soluble paper in use for hair color treatments include but are not limited to:
1. The ability to withstand the heat of the coloring or highlight process without becoming flammable;
2. The ability to wash out of the hair in the rinsing process, thus eliminating the need for removal from the hair like foil, and eliminating conventional trash-to-landfill disposal while complying with environmental laws; and
3. The ability of improve the sheen, luster and softness of the hair to which it is applied.
4. Reduces the need for additional products customarily applied to enhance sheen, gloss or softness. Reduction of these products further improves environmental impact and exposure of the user to harmful free-radicals commonly known to be present in such enhancing products.

When additional ingredients are added to the paper for the purpose of creating additional sheen or softness, the unique attribute #4 is not diminished. It is enhanced by the lower quantities of such products required to achieve the same or better result.
5. Improves the speed with which a professional stylist can complete a hair coloring or highlighting treatment.

(How The Invention Functions) For a person skilled in the art of hair coloring or highlighting, or a consumer purchasing a product for self-application, the process is the same as a traditional hair color or highlight treatment, with the exception of the following:
1. The use of a foil sheet is replaced with the use of the water soluble paper, and essentially used in the same way the foil sheet would be used: and
2. At the conclusion of the treatment, instead of removing the paper as one would do with a foil sheet(s), the hair is simply rinsed of the hair solution, and the paper simultaneously dissolves, hence being rinsed down the drain.

A summary of the commonly followed procedure for hair highlighting or applying hair color is as follows:
1. Place the coloring or highlight product on the hair.
2. Weave fine strands of hair and place them along the length of the water soluble paper.
3. Separate the hair when laying it down on the paper.
4. Place another water soluble paper on top of the same hair or it can be folded depending on the length of hair, and depending on the intended outcome. You can use one sheet of paper and fold but it depends on the stylist if they like to fold or lay another sheet over the hair.
5. Lay the combined water soluble papers with hair in between as close to the head as possible.
6. Repeat for as many times throughout the hair as necessary to complete the intended hair treatment.

What is claimed is:

1. A method of coloring for coloring hair comprising the steps of:
   a) positioning at least one sheet of foldable, biodegradable water soluble cellulosic paper in the absence of added implements, on a head of a person;
   b) placing small amounts of hair on the paper and applying a hair color treatment solution to the hair;
   c) securing the paper around the hair to form a pouch wherein the solution and hair are secured within the paper, and wherein further the paper is devoid of adhesive to secure the pouch;
   d) applying pressure to the pouch to ensure even coverage of the solution to the hair and adhere the hair to the paper;
   e) waiting a sufficient period of time to allow the solution to color the hair; and,
   f) rinsing the hair with water, simultaneously removing the solution and the paper from the head of the person.

2. The method of claim 1 wherein the hair is heated for a period of time between about 30 minutes to about 60 minutes.

3. The method of claim 1 wherein a heat lamp is utilized.

4. The method of claim 1 wherein the paper is substantially triangular, planar, about 4 inches to about 6 inches in width, and about 6 inches to about 12 inches in length.

5. The method of claim 1 wherein the paper comprises sodium carboxyl methy cellulose and wooden pulp.

\* \* \* \* \*